(12) United States Patent
Laragh

(10) Patent No.: US 6,595,926 B1
(45) Date of Patent: Jul. 22, 2003

(54) METHOD FOR EVALUATING AND TREATING HYPERTENSION

(76) Inventor: John H. Laragh, 5 Sandpiper Dr., Golf, FL (US) 33436

( * ) Notice: Subject to any disclaimer, the term of this patent is extended or adjusted under 35 U.S.C. 154(b) by 0 days.

(21) Appl. No.: 09/860,199

(22) Filed: May 17, 2001

Related U.S. Application Data

(63) Continuation-in-part of application No. 09/657,027, filed on Sep. 7, 2000.

(51) Int. Cl.[7] .............................. A61B 5/02; A61K 49/00

(52) U.S. Cl. ..................... 600/481; 600/483; 600/300; 424/9.1; 424/9.2

(58) Field of Search .................................. 600/481, 483, 600/484, 485, 486, 490, 479, 454, 300, 301; 424/9.1, 9.2

(56) References Cited

U.S. PATENT DOCUMENTS

| 4,080,966 A | | 3/1978 | McNally et al. ............ 128/214 |
| 4,425,920 A | | 1/1984 | Bourland et al. ........... 128/672 |
| 4,911,909 A | * | 3/1990 | Reilly ..................... 424/141.1 |
| 5,687,731 A | | 11/1997 | Ragozin et al. ............. 128/672 |
| 5,830,131 A | | 11/1998 | Caro et al. .................. 600/300 |
| 5,849,773 A | * | 12/1998 | Hanson et al. .............. 514/365 |
| 5,938,626 A | * | 8/1999 | Sugerman ................... 600/561 |
| 5,942,548 A | * | 8/1999 | Hanson et al. ........... 514/252.1 |
| 6,063,805 A | | 5/2000 | Oxenkrug et al. |

OTHER PUBLICATIONS

Blumenfeld, Jon D., et al. "Plasma Renin Activity in the Emergency Department and Its Independent Association With Acute Myocardial Infarction," American Journal of Hypertension, Ltd. 2000, 855–863, Elsevier Science.

Laragh, John H., "The Role of Biochemical Markers in the Assessment and Management of Hypertension," 1994, Planned and Produced in accordance with the ACCME Essentials on Enduring Materials.

Blumenfeld, Jon D., et al. "Renin System Analysis: A Rational Method for the Diagnosis and Treatment of the Individual Patient With Hypertension," American Journal of Hypertension, 1998, Elsevier Science.

Trilling, Jeffrey S., et al, "The Urgent Need to Improve Hypertension Care," Archives of Family Medicine, 2000, 794–801, vol. 9 No. 9.

* cited by examiner

Primary Examiner—Max F. Hindenburg
Assistant Examiner—Navin Natnithithadha
(74) Attorney, Agent, or Firm—Kramer, Levin, Naftalis & Frankel LLP

(57) ABSTRACT

The Laragh Method is a novel method useful for evaluating and treating hypertensive patients. The Laragh Method provides a systematic approach for the physician to use volume vasoconstriction information with entry and induced changes in blood pressure and in ambulatory plasma renin levels for the rational selection of treatment tailored to suit each individual hypertensive patient. The Laragh Method provides a systematic and rational approach to drug selection which greatly improves the therapeutic success rate among hypertensive patients and which for the large majority provides long-term blood pressure control with one drug instead of two or two instead of three with each drug rationally targeted to control the renin and/or volume elements in the blood pressure equation.

13 Claims, 8 Drawing Sheets

METHOD FOR EVALUATING AND TREATING HYPERTENSION

A METHOD FOR EVALUATING AND TREATING HYPERTENSION

This application is a continuation-in-part of U.S. application Ser. No. 09/657,027, filed Sep. 7, 2000.

FIELD OF THE INVENTION

The present invention relates to new and useful methods for the evaluation and treatment of hypertension.

BACKGROUND INFORMATION

Hypertension is a sustained elevation of blood pressure that can lead to heart attack, heart or kidney failure, stroke, and other cardiovascular diseases. Hypertension affects about 20% of the population worldwide. A major problem is that the current methods that are widely used for the detection and treatment of hypertension are inadequate and result in enormous personal suffering and economic costs.

The Economic Costs of Hypertension

The 1999 Annual Report of the American Heart Association estimates the direct cost of hypertension in the United States to be $26.1 billion annually, plus an additional $11.1 billion in indirect costs arising from lost productivity due to morbidity and mortality (Table 1). Moreover, the link between hypertension and other cardiovascular diseases has become increasingly evident.

adequately controlled. A more conservative estimate suggests that this rate may be as low as 12%, and in other countries, the treatment success rates may be even lower: 12% in France, and 9% in Britain. Moreover, the available data indicate that the success rate of treatment has actually fallen during the past several years, despite the availability of new and powerful antihypertensive medications.

Poor success rates in the management of hypertensive patients have resulted from empirical approaches to selecting antihypertensive drugs. This empirical approach is recommended by.authorities, and followed by many Physicians. For example, in the United States, the Joint National Committee (JNC) on Prevention, Detection, Evaluation, and Treatment of High Blood Pressure periodically surveys the literature and current knowledge on hypertension. The current recommendation of the JNC (JNC VI) is to use a diuretic or a β-blocker—among the oldest classes of antihypertensive drugs—as a first line treatment.

The recommendations of the JNC VI are based on a traditional epidemiological model in their evaluation of hypertension treatment. In this model, hypertension is assumed to be a single process disease in which all patients have a common pathophysiological mechanism. When blood pressure does not decrease in response to empirical treatments with either diuretics or β-blockers or both, several different drug types are added until blood pressure is subdued. This empirical approach to treatment is referred to as "stepped care". Stepped care results in many patients being treated with at least two different antihypertensive drug types. This approach tends to increase the long term

TABLE 1

Economic Costs of Hypertension in the U.S. ($ Billion)

|  | Heart Disease | Coronary Artery Disease | Stroke | Hypertension | Congestive Heart Failure | Total Cardio-Vascular Disease |
|---|---|---|---|---|---|---|
| Direct Costs | | | | | | |
| Hospital/Nursing Home | $ 78.9 | $ 42.0 | $25.0 | $ 7.4 | $15.5 | $128.4 |
| Physicians/Other Professionals | 14.4 | 8.1 | 2.3 | 8.1 | 1.5 | 28.2 |
| Drugs | 7.3 | 3.5 | 0.4 | 9.0 | 1.1 | 17.7 |
| Home Health/Other Medical Durables | 5.2 | 1.6 | 2.9 | 1.6 | 2.2 | 11.5 |
| Total | $105.9 | $ 55.2 | $30.6 | $26.1 | $20.3 | $185.8 |
| Indirect Costs | | | | | | |
| Lost Productivity/Morbidity | 17.2 | 7.2 | 5.6 | 5.2 | NA | 27.6 |
| Lost Productivity/Mortality | 91.6 | 55.8 | 15.1 | 5.9 | 2.2 | 113.2 |
| Grand Total | $214.7 | $118.2 | $51.3 | $37.2 | $22.5 | $326.6 |

Source: American Heart Association 1999 Annual Report

Number Affected and the Low Rate of Treatment Success

It is estimated that in the United States alone there are about 50 million hypertensives, of whom only about 68% have had their hypertension diagnosed (Table 2). Among the estimated 34.2 million identified hypertensives receiving medical treatment, only 27% have their blood pressure expense of treatment and to promote more adverse side effects. Perhaps consequently, only a small proportion of patients complies with their antihypertensive drug regimen, which further reduces the possibility of achieving blood pressure control. For example, a recent study in California showed that only 6% of the hypertensive Medicaid population adhere to their drug treatment regimens.

TABLE 2

Detection and Treatment of Hypertension in the US

|  | 1988–1991 | 1991–1994 |
|---|---|---|
| Awareness | 73% | 68% |
| Treatment | 55% | 54% |
| Control | 29% | 27% |

Source: Joint National Committee on Prevention, Detection, Evaluation, and Treatment of High Blood Pressure (JNC VI)

Therefore, a great need exists for methods to successfully evaluate and treat hypertensive patients in order to reduce both the enormous cost associated with hypertension, and consequential costs of cardiovascular diseases, which is estimated at about 15% of the $1.2 trillion annual US Health Care bill.

SUMMARY OF THE INVENTION

The present invention discussed herein provides novel methods or systems—the Laragh Method—for evaluating and treating hypertensive patients. The Laragh Method provides a systematic approach that allows physicians and other health care providers to select the appropriate treatment, tailored to suit each individual hypertensive patient. The Laragh Method greatly improves the therapeutic success rate among hypertensive patients and uses more rational drug selection as compared to the traditional, empirical "stepped care" approach.

The stepped care approach is conceptually flawed because it fails to recognize the heterogeneity of biochemical mechanisms involved among different hypertensive patients. The Laragh Method incorporates the concept that high blood pressure, like fever, is a physical sign that has several identifiable causes and underlying abnormal mechanisms. Just as fever cannot be appropriately treated with a single recipe, neither should hypertension.

Unlike the recommendations of the JNC, which are based partly on the preconception of a single process and other epidemiological considerations, the Laragh Method evaluates and treats the identifiable pathogenic mechanisms that caused blood pressure to rise in the individual patient in the first place.

The Laragh Method can be used to evaluate and treat previously untreated hypertensive patients as well as patients who have undergone or are receiving unsuccessful treatments. In addition, the Laragh Method may be used to evaluate and treat hypertensive crises.

DETAILED DESCRIPTION

Figure 1:
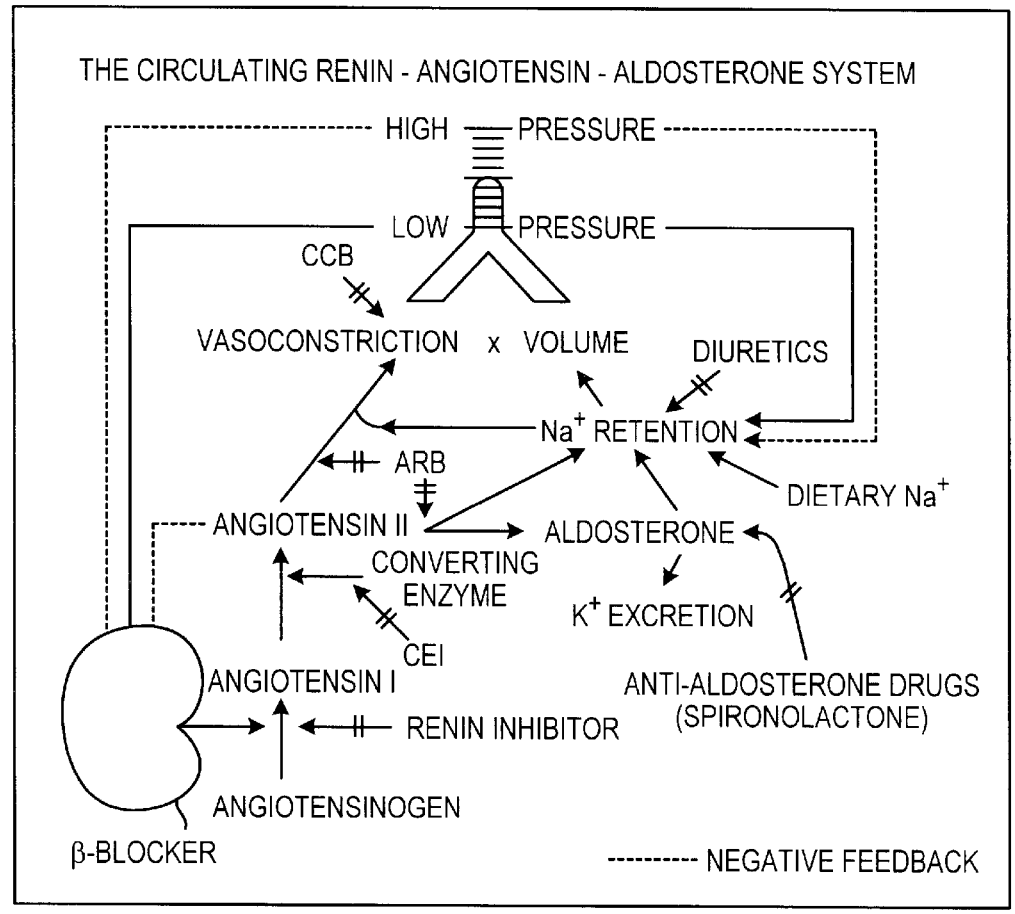
FIG. 1 illustrates the renin-angiotensin-aldosterone system.

FIG. 1 is a schematic illustration of the renin-angiotensin-aldosterone system. The normal function of this system is generally believed to raise blood pressure when it is too low and thus maintain blood pressure during upright posture and exercise or during periods of dehydration or salt loss. However, excessive kidney renin secretion, leading to higher plasma renin levels, is associated with hypertension, heart attack, stroke, and other cardiovascular disease.

Mechanisms of Blood Pressure Control and Antihypertensive Drugs

Blood pressure is determined to a large extent by a combination of two factors: the size of the blood volume and the degree of constriction of arterioles, small muscular blood vessels at the periphery of the vasculature. Blood volume is determined largely by the amount of sodium in the body, which osmotically retains fluid in the body and thereby enlarges the blood volume. The constriction of arterioles is controlled by several factors, the most important of which is the amount of renin circulating in the blood. Renin is a hormone released by the kidney into circulation. Renin's only known action is to enzymatically release angiotensin I, a decapeptide, from circulating angiotensinogen. Angiotensin I has no pressor action but it is rapidly "converted" to an octapeptide, angiotensin II, by converting enzymes lining blood vessel walls and circulating in the bloodstream. Angiotensin II causes the blood vessels to constrict. Thus, blood pressure is elevated when the plasma levels of renin-angiotensin or the body sodium content are excessive.

The release of renin into the blood is the first step in a rapid sequence of events that raises blood pressure:

In normotensive individuals, renin secretion is stimulated either by a fall in blood pressure or low blood volume, the latter usually caused by salt depletion. Conversely, the renin system is normally turned off by higher blood pressures or salt intake.

Renin acts on a plasma protein (angiotensinogen) to release angiotensin I, which is then converted by angiotensin converting enzyme (ACE) in blood vessel walls into angiotensin II.

Angiotensin II instantly constricts the blood vessels, thus maintaining or elevating blood pressure.

Angiotensin II also stimulates the adrenal glands to produce aldosterone, that causes salt retention that raises blood volume and flow to restore blood pressure.

When blood pressure and blood volume have been restored, kidney renin secretion is turned off by the improved blood flow to the kidneys.

In normotensives, there is always a reciprocal relationship between salt intake and plasma renin. As salt intake and blood pressure rise, plasma renin activity falls. Conversely, when salt intake falls, plasma renin levels rise. However, in hypertensives, plasma renin levels may be elevated despite normal salt intake and despite elevated blood pressure. Because elevated blood pressure should turn off renin secretion, any amount of plasma renin in a hypertensive individual is abnormal. Only in low-renin hypertensive patients does renin release behave normally, and in them, blocking renin activity will have no effect on blood pressure. In hypertensive patients with "normal" or high plasma renin levels, the kidney renin behaves abnormally because in normal people a high salt intake or a higher blood pressure will promptly "turn off" kidney renin release and plasma renin will fall to zero. This is proved by the fact that blocking plasma renin in normal and high renin hypertensives will promptly correct their hypertension.

The Laragh Method approach to the management of hypertensive patients recognizes that hypertension can result from a spectrum of conditions ranging from those that are largely volume-dependent (sodium mediated) to those that are largely vasoconstriction-dependent (renin angiotensin-mediated). The available antihypertensive drugs all act to curtail either the sodium factor or the renin factor. Knowing the plasma renin or angiotension level, the Laragh Method can be used to select the right drug type to treat the specific mechanisms that underlie the hypertension in each individual patient.

The Laragh Method provides a framework for exposing and understanding the failures of widely used antihypertensive strategies. For example, when the vasoconstriction (i.e., renin) arm of the blood pressure control system is blocked by antihypertensive medication, reactive increases in the activity of the renin system can occur that blunt the efficacy of the drug. Compensatory changes can also occur so that blocking one mechanism will cause an increase in the activity of the other component (i.e., vasoconstriction or volume) such that blood pressure remains elevated. Together, these two offsetting reactions can further reduce the effectiveness of an antihypertensive drug program.

Because empirical approaches to antihypertensive therapy are population based and fail to select drugs for the individual patient based on the mechanism of their disease, a patient could receive a drug for life which is ineffective in controlling his or her blood pressure. Further, even if the right drug is fortuitously prescribed, the reactive and compensatory changes that occur during treatment may overcome, or mitigate the effects of the drug. This leads to further unguided excessive manipulations of antihypertensive medication programs.

Two Basic Types of Hypertensive Patients

The pharmacologic treatment of the hypertensive patient is a complex decision-making process. It is complicated by the fact that there are many pharmacologically distinct drug classes available and that hypertensive patients are not all alike mechanistically so that individual hypertensive patients respond quite differently to the various different types of anti-hypertensive drugs, Diuretics, specific aldosterone receptor blockers, calcium channel blockers, alpha blockers, beta blockers, ACE inhibitors, angiotensin receptor blockers and centrally acting alpha agonists, comprise the major categories. The problem of which drug to chose for a particular patient is further complicated by the availability of many different products within these classes, which are often claimed by their maker to differ importantly from other products in the same class. Such marketing claims further confuse physicians and patients.

The Laragh Method overcomes these problems by classifying hypertensive patients into two major categories based on PRA (plasma renin-angiotensin) levels: (1) those with PRA levels<0.65 ng/ml/hr who have predominantly sodium-volume mediate hypertension, and (2) those with PRA levels≧0.65 ng/ml/hr who have predominantly and progressively more plasma renin-angiotensin mediated vasoconstrictor hypertension.

TABLE 3

TWO BASIC TYPES OF HYPERTENSIVE PATIENTS

| | |
|---|---|
| PRA levels < 0.65 ng/ml/hr: | Have predominately sodium-volume mediated hypertension |
| PRA levels ≧ 0.65 ng/ml/hr: | Have predominately plasma renin-angiotensin mediated vasoconstrictor hypertension |

Two Types of Drugs

The Laragh Method simplifies the approach to treatment by classifying the available anti-hypertensive drug classes according to their major mode of action into two major categories:

Drugs that lower blood pressure by reducing or blocking the activity of the renin-angiotensin system.

Drugs that reduce blood pressure because of primary or secondary actions to reduce body sodium and volume content by enhancing renal sodium excretion.

TABLE 4

TWO BASIC TYPES
OF ANTIHYPERTENSIVE DRUGS

Anti-Na$^+$-Volume "V" Drugs
Primary

Thiazide and Loop Diuretics
SARA,* e.g., Spironolactone
Secondary

α-Blockers
Ca$^{2+}$ Antagonists (CCB)
Anti-Renin-Angiotensin "R" Drugs

ACE Inhibitors (block A$_{II}$ Formation)
Ang II Receptor Blockers (ARB) (block A$_{II}$ action)
β-Blockers (reduce kidney renin secretion)

*Specific Aldosterone Receptor Antagonists

The drugs listed below and the accompanying dosage ranges are exemplary and are not intended to limit the drugs or dosages which may be used in the Laragh Method.

Anti-Sodium Volume "V" Drugs

Included in this category are the drugs that have a primary natriuretic action on the kidneys, i.e., they reduce body sodium and water content. In general, diuretics work by preventing reabsorption of salt and water from renal tubular urine by the kidneys. Thus, the sodium and water content in the body decreases leading to falls in cardiac output (the amount of blood the heart pumps) and later followed by a reduction in total peripheral resistance (the degree to which blood vessels are constricted and, thus, resist blood flow). Both changes contribute to salt depletion arid drop in blood pressure. Drugs in this class include the thiazide or loop diuretics, and the specific aldosterone receptor antagonists (SARA), which have potent natriuretic-diuretic action without K$^+$ loss, while also blocking other effects of the hormone aldosterone mediated by its receptors. A second class of natriuretic-diuretic drugs involves agents which may have another primary anti-hypertensive action but which also act on the kidneys to promote natriuresis. Thus, the calcium channel blockers (CCB) lower blood pressure by reducing intracellular calcium levels in the small blood vessel walls, but also have a natriuretic effect because of their renal vasodilatation. The alpha blockers reduce alpha adrenergic vasoconstrictor effects and promote natriuresis. These drugs block alpha receptors in the arteries and prevent norepinephrine from reaching receptors in the heart and kidneys which results in vasodilatation and a concomitant reduction in blood pressure. These CCBs and alpha blockers are not classical anti-sodium volume drugs, but they are included in the anti-volume drug group because their natriuretic effects have been shown to facilitate their anti-hypertension action and to make them especially effective in low renin-high volume hypertensive patients. Other drugs that may be discovered or developed in the future may also be used as V drugs if they have similar mechanisms of action or act similarly to other V drugs in the Laragh Method.

Diuretics

Available diuretics include, but are not limited to, thiazides, loop diuretics, SARA drugs, and combination drugs. Thiazides include, but are not limited to, the following: bendroflumethiazide (Naturetin), 2.5 to 5.0 milligrams per day; chlorothiazide (Diuril) 125 to 500 milligrams per day; chlorthalidone, (Hygroton, Thalitone) 12.5 to 50 milligrams per day; hydrochlorothiazide (Esidrix, HydroDIURIL, Oretic) 12.5 to 50 milligrams per day; indapamide (Lozol) 2.5 to 5.0 milligrams per day; methylclothiazide (Enduron) 2.5 to 5.0 milligrams per day; and metolazone (Zaroxolyn, Mykrox) 0.5 to 5.0 milligrams per day.

Loop diuretics include, but are not limited to, bumetanide (Bumex) 0.5 to 5.0 milligrams per day; ethacrynic acid (Edecrin) 25 to 100 milligrams per day; and furosemide (Lasix) 20 to 320 milligrams per day.

Specific aldosterone receptor antagonists (SARA's) reduce sodium and water content of the body but prevent excessive loss of potassium in urine. These SARA drugs include, spironolactone (Aldactone) 12.5 milligrams per day.

Combination drugs are available which comprise traditional diuretics together with a SARA drug. They include Spironolactone with Hydrochlorothiazide (Aldactazide) 50 to 100 milligrams per day.

Secondary V Drugs

The so-called secondary V drugs include calcium channel blockers and alpha blockers. Traditional calcium channel blockers include, but are not limited to, the following: amlodipine (Norvasc) 2.5 to 10.0 milligrams per day; diltiazem (Cardizem) 90 to 360 milligrams per day; diltiazem-sustained release (Cardizem SR) 120 to 360 milligrams per day; Diltiazem-extended release (Dilacor XR) 180 to 360 milligrams per day; Felodipine-sustained release (Plendil Extended Release) 5 to 10 milligrams per day; Isradipine (DynaCirc) 2.5 to 10.0 milligrams per day; Nicardipine-sustained release (Cardene SR) 60 to 120 milligrams per day; Nifedipine (Adalat, Procardia) 30 to 120 milligrams per day; Nifedipine-sustained release (Adalat CC, Procardia XL) 30 to 90 milligrams per day; Verapamil (Calan, Isoptin) 80to 360 milligrams per day; and Verapamil-long acting (Calan SR, Isoptin SR, Verelan) 120 to 360 milligrams per day.

Secondary V drugs also include newer calcium channel blockers including, but not limited to, Diltiazem-sustained release (Tiazac); Nisoldipine (Sular); Verapamil-extended release (Coveta-HS), Lacidipine (succeeded in early drug trials and may be available soon); and Manidipine (available in Europe).

Secondary V drugs also include alpha blockers. Available alpha blockers include, but are not limited to, the following: doxazosin (Cardura) 1 to 16 milligrams per day; labetalol (Normodyne, Trandate) 200–1,200 milligrarms per day; prazosin (Minipress) 1 to 20 milligrams per day; and terazosin (Hytrin) 1 to 20 milligrams per day.

The Effect of V Drugs on PRA Levels

It is important to understand that there is a reciprocal relationship between PRA and blood pressure. High blood pressure suppresses renin secretion whereas low blood pressure increases renin secretion. PRA levels should fall when hypertension initially develops in hypertensive patients. This effect of high blood pressure to lower renin explains why many hypertensive patient do in fact have subnormal blood renin levels. Reciprocally, effective therapy to lower blood pressure usually causes the PRA to rise because the falling blood pressure stimulates renin secretion. This means that if the PRA level in a patient does not increase during treatment (with any antihypertensive drug other than a beta blocker, or centrally acting adrenergic drugs that act by lowering renin secretion), the drug is either not effective, or the dose is too small, or the patient is not taking the drug. Over and above the stimulatory effects on renin of a fall in blood pressure, the natriuresis induced by diuretics or by the specific aldosterone receptor antagonists also increases PRA levels by turning turn off a signal from the macula densa region of the nephron. This dual action means that when diuretics or SARAs lower blood pressure, PRA levels are likely to increase to a greater extent than they do when hypertension is corrected by the other anti-volume drugs, the calcium channel blockers (CCBs) or alpha blockers.

Figure 2:
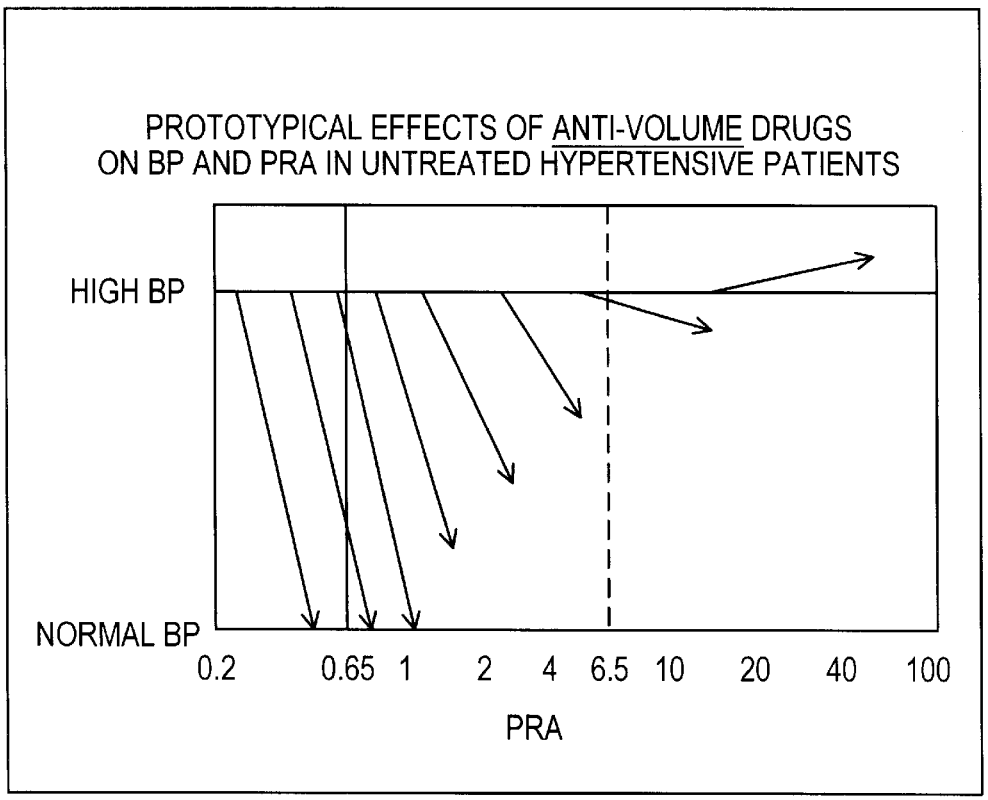
FIG. 2 illustrates the typical effects of anti-volume drug types, as defined by the Laragh Method, on blood pressure; and on plasma renin activity in previously untreated hypertensive patients.

FIG. 2 shows the expected changes in BP and plasma renin levels induced by anti-volume drugs in hypertensive patients in relation to their baseline PRA levels. Note that the PRA levels are shown on a logarithmic scale. The left hand-side of the arrows indicate the BP and PRA levels of untreated patients. The head of the arrows indicate the BP and PRA levels of the same patients during treatment.

As indicated in FIG. 2 anti-volume drugs are most effective in patients with PRA<0.65 ng/ml/hr. Such patients usually have only a small reactive rise in PRA levels. The Laragh Method incorporates these observations.

Patients with PRA levels equal to or greater than 0.65 ng/ml/hr are likely to have a lesser fall in BP as they may have both volume and vasoconstrictor components to their blood pressure.

As PRA levels rise, patients are less and less likely to respond to anti-volume drugs since they are likely to have less and less of a volume component and more of a renin component to their BP. Moreover, the higher the baseline PRA the more likely that V drugs will induce a large reactive rise in PRA levels. Because the higher PRA level is more vasculotoxic, these patients are unlikely to gain any cardio-protection, even if the diuretic induces a small fall in blood pressure.

Renovascular hypertension should always be considered as a possible diagnosis in any patient with baseline PRA levels>1.5 ng/ml/hr. In some renovascular hypertensive patients blood pressure may actually rise further during diuretic therapy because of their very large reactive rises in renin secretion and thus plasma renin levels.

Anti-Renin "R" Drugs

Anti-renin "R" drugs either (1) reduce the kidney secretion of renin (beta blockers), (2) prevent angiotensin II from being formed by renin (angiotensin converting enzyme inhibitors), or (3) prevent angiotensin II from engaging its receptor in the blood vessel wall (angiotensin receptor blockers). Thus, all three act at different points to impair renin system function. All three, however, are less than complete blockers of the renin-angiotensin system. Therefore, and because they block the renin system at different points, all three can be used in combinations with each other to more completely block the renin system in resistant patients. Other drugs that may be discovered or developed in the future may also be used as R drugs if they have similar mechanisms of action or act similarly to other R drugs in the Laragh Method.

Available beta-blockers which can be incorporated into the Laragh Method include, but are not limited to, the following: acebutolol (Sectral) 200 to 1,200 milligrams per day; atenolol (Tenormin) 25 to 100 milligrams per day; betaxolol (Kerlone) 5 to 40 milligrams per day; Carteolol (Catrol) 2.5 to 10.0 milligrams per day; Metoprolol (Lopressor) 50 to 200 milligrams per day; Metoprolol-extended release (Toprol-XL) 50 to 200 milligrams per day; Nadolol (Corgard) 20 to 240 milligrams per day; Penbutolol (Levatol) 20 to 80 milligrams per day; Pindolol (Visken) 10 to 60 milligrams per day; Propranolol (Inderal) 5 to 240 milligrams per day; Propranolol-long acting (Inderal LA) 60 to 240 milligrams per day; and Timolol (Blocadren) 20 to 40 milligrams per day.

Several newer beta blockers are available and include, but are not limited to, the following: carvedilol (Coreg); Nebivolol; celiprolol.

In addition to the beta blockers, other R drugs, such as angiotensin converting enzyme inhibitors (ACE inhibitors) may be used in the Laragh Method. ACE is an enzyme that catalyzes the conversion of an inactive substance, angiotensin I into angiotensin II, a powerful vasoconstrictor. ACE inhibitors inactivate this enzyme and reduce the amount of angiotensin II in the blood, thereby resulting in vasodilatation and lower blood pressure. Among the available ACE inhibitors are the following: benazepril (Lotensin) 10 to 40 milligrams per day; Captopril (Capoten) 12.5 to 150 milligrams per day; enalapril (Vasotec) 2.5 to 40 milligrams per day; Fosinopril (Monopril) 10 to 40 milligrams per day; Lisinopril (Prinivil, Zestril) 5 to 40 milligrams per day; Quinapril (Accupril) 5 to 80 milligrams per day; Ramipril (Altace) 1.25 to 20 milligrams per day; Trandolapril (Mavik) 1 to 4 milligrams per day; and Moexipril Hydrochloride (Univasc) 7.5 to 60 milligrams per day.

Another class of R drugs are the angiotensin receptor blockers (ARB). These drugs block the ability of angiotensin II to constrict the arteries. Angiotensin receptor blockers include, but are not limited to, Irbesartan (Avapro) 150 to 300 milligrams per day; Losartan (Cozaar) 50 to 200 milligrams per day; and Valsartan (Diovan) 80 to 320 milligrams per day.

The Effect of R Drugs on PRA

Over and above the stimulatory effects on kidney renin release of an induced fall in blood pressure, ACE inhibitors (CEI), and angiotensin receptor blockers (ARB) also directly increase PRA levels. The CEIs and ARBs increase PRA because, by preventing either the formation of angiotensin II or its actions, they cripple the naturally operating feed-back suppression of increased plasma angiotensin II levels on renal renin secretion. That means that when either CEIs or ARBs lower blood pressure, PRA levels increase much more than when hypertension is corrected with calcium channel blockers or alpha blockers.

As indicated, beta blockers and centrally acting suppressors of the sympathetic nervous system such as clonidine are the special case. These two groups are the only class of antihypertensive drugs that lower PRA levels. They both do so either by blocking or reducing the beta sympathetic stimulation of kidney renin secretion. In this way they are remarkably effective for lowering plasma renin and angiotensin II levels. It is important to know, however, that, because they only suppress renin secretion via the beta receptor, renin levels may not be completely suppressed PRA levels. If the excessive secretion of renin in a particular hypertensive patient is mediated by another mechanism (e.g., kidney disease), beta blockers will still lower PRA levels, but may not reduce them enough to optimally lower blood pressure. However, because beta blockers powerfully lower renin secretion they are also extremely useful in combination with the other anti-renin drugs because they blunt the reactive rise in renin which otherwise can overcome the renin system blockade induced by CEI or ARB treatment. Thus, by reactively secreting more and more renin, a patient can sometimes overcome the blockade of angiotension II formation (CEI) or action (ARB) and the blood pressure goes back up.

Figure 3:
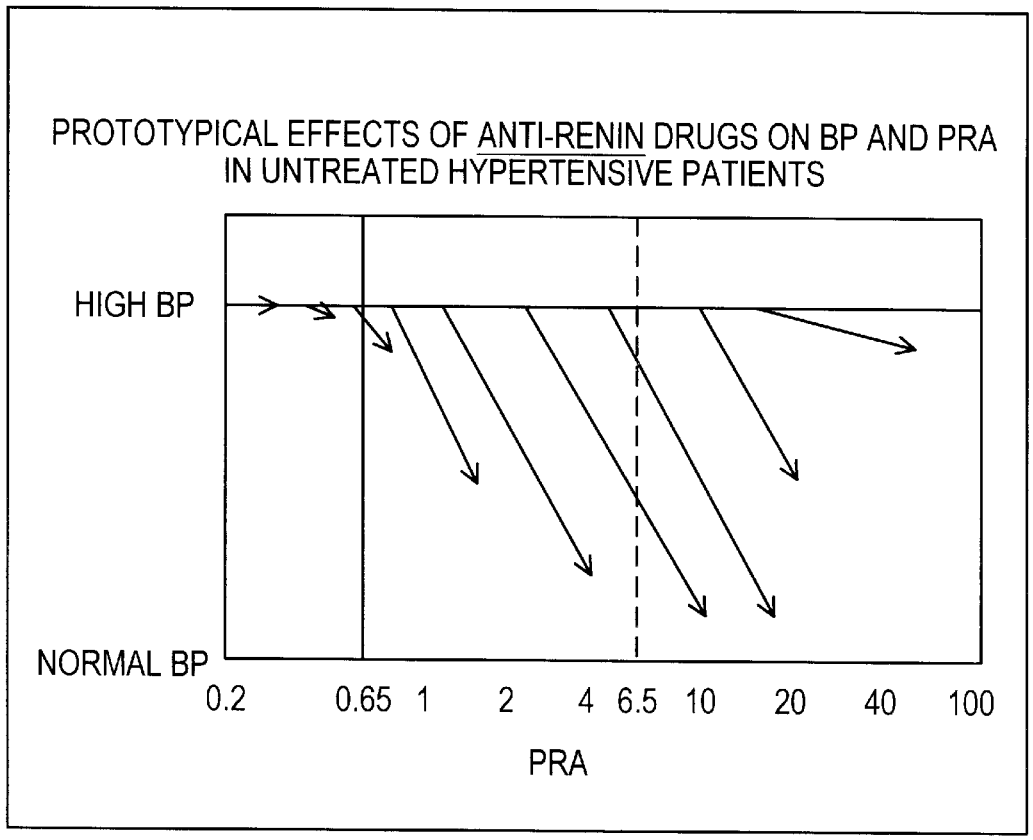
FIG. 3 illustrates the typical effects of the anti-renin drug types defined by the Laragh Method on blood pressure and on plasma renin activity in previously untreated hypertensive patients.

FIG. 3 shows the expected changes in BP and plasma renin levels induced by anti-renin drugs (i.e., "R drugs") in hypertensive patients in relation to their baseline PRA levels. Note that the PRA levels are shown on a logarithmic scale.

Patients with PRA levels less than 0.65 ng/ml/hr are unlikely to have a fall in BP with anti-renin system drugs because plasma renin levels are too low to support the blood pressure. Accordingly too, their PRA levels are unlikely to increase much on anti-renin drug therapy.

Between PRA levels of 0.65 and 6.5 ng/ml/hr, the higher the baseline PRA level the more likely that blood pressure will fall and the greater the likely fall in BP with anti-renin system treatment.

Above a PRA level of about 6.5 ng/ml/hr (10 times the level at which circulating PRA levels begin to affect blood pressure) the blood pressure response to monotherapy with anti-renin drugs such as CEIs and ARBs may become less because when they lower pressure they always induce a reactive rise in renin. Since most anti-renin system drugs block only about 90% of the circulating renin-angiotensin system, a 10 fold rise in PRA levels can completely overcome anti-renin system blockade. Since renin secretion is likely to be most reactive in patients with very high baseline renin levels, the blood pressure of a few patients with exceptionally high plasma renin levels, who are at greatest need for anti-renin system therapy, may not respond adequately to a single R drug. However, their PRA level will indicate a dramatic response. They need two or more anti-renin system drugs.

In this regard, beta blockers, because they also curtail a reactive rise in, PRA, are often useful adjuncts to ACE inhibitors and angiotensin receptor blockers. ACE and ARBs are also good in combination since they each attack the renin system at different locations.

The lack of any PRA rise in a patient taking an ACE or ARB is an important piece of information. It tells you that the drug is not working. The reason is either non-compliance or lack of sufficient drug (dose too low) or too low a baseline renin level.

Renovascular hypertension should always be considered in any patient with baseline or treatment PRA levels of 1.5 ng/ml/hr, or with a large reactive rise in PRA after CEI or ARB treatment.

Combination Therapy

For those patients who have both a renin and a sodium factor, either primary, or reactive to the first drug, combination therapy using one or more anti-renin and/or anti-volume drugs may prove necessary. For such patients, two-drug combinations are possible and might prove effective and suitable. Alternatively, combination therapy may be used consisting of only two single drugs which involve both V and R pharmacological agents (V/R drugs). Thus, the Laragh Method described herein may accommodate the rational application of a single V/R combined drug.

The demonstration of the efficacy of any combination should be demonstrated in each patient by renin and blood pressure testing. Once the combination regimen has been verified using single drugs, one of the many combination pills commercially available may be used for convenience to reduce the number of tablets required.

Thus, various combinations of beta-blocker and diuretics, for example, may be used as a single drug combination treatment regimen. Such drugs include, for example, the following: Atenolol,(Tenormin) with Chlorthalidone; Nadolol 40–80 milligrams per day with Bendroflumethiazide 5–10 milligrams per day (Corzide); and Propranolol Hydrochloride with Hydrochlorothiazide (Inderide).

Another combination treatment is, for example, a drug which combines an ACE inhibitor and a diuretic. Such currently available drugs include, but are not limited to: Captopril with Hydrochlorothiazide (Capozide), individualized dosing; Enalapril 5 milligrams per day with Hydrochlorothiazide 12.5 milligrams per day (Vaseretic); Lisinopril 10–80 milligrams per day with Hydrochlorothiazide 6.25–50 milligrams per day (Zestoretic); and Moexipril Hydrochloride <30 milligrams per day with Hydrochlorothiazide 50 milligrams per day (Uniretic).

Yet another combination treatment comprises the combination of an ACE inhibitor and a calcium channel blocker. Such drugs include, but are not limited to: Amlodipine>2.5 milligrams per day with Benazepril Hydrochloride 10 milligrams per day (Lotrel); Enalapril with Felodipine (Lexxel); and Trandolapril 1–4 milligrams per day with Verapamil hydrochloride 180–240 milligrams per day (Tarka).

Also available are formulations which combine an angiotensin blocker and a diuretic. Such drugs include, for example, Losaitan potassium 50–100 milligrams per day with Hydrochlorothiazide 1.25–25 milligrams per day (Hyzaar).

Other classes of Drugs

Other classes of drugs such as central alpha agonists, for example, may be incorporated into the Laragh Method. Available alpha agonists include: Methyldopa (Aldomet) 500–2,000 milligrams per day; Clonidine (Catapres) 0.2 to 0.4 milligrams per day; Ser-Ap-Es; Guanfacine hydrochloride (Tenex) 1 to 2 milligrams per day; and Guanabenz acetate (Wytensin) 4 to 8 milligrams per day. Because of unpleasant side effects, these drugs are rarely recommended.

In addition, drugs which have not yet been developed but which will exhibit properties of a V drug, an R drug, or a.combination V/R drug may be incorporated into the Laragh Method.

Central Importance of the Plasma Renin Activity Test

The plasma renin activity test (PRA) measures the capacity of the renin in the patients blood to form angiotensin in the bloodstream, which acts directly and immediately on the small blood vessels to constrict them and raise blood pressure accordingly. A properly performed enzyme kinetic plasma renin assay is therefore crucial and central for assessment of plasma renin-angiotensin involvement in hypertension and other related cardiovascular disorders.

The test may be performed by collecting 7 ml or less of venous blood in an EDTA Vacutainer® from a quietly seated ambulatory patient. Fasting or special diets are not required. The blood is collected and stored at room temperature and is not chilled. After separation, the plasma is stored at room temperature until the assay is performed in the next day or two. For delayed analyses, plasma is frozen and then rapidly thawed for analysis. The details of the analytical procedure for the enzyme kinetic method for measuring renin have been published in J. E. Sealey Clinical Chemistry 1991 and by Sealey, James and Laragh 1995 in Laragh and Brenner Second Edition, Hypertension: Pathophysiology, Diagnosis and Management, Laragh J. H. and Brenner, B. N., (eds.), Raven Press, New York, N.Y., pp. 1953–1968, the contents of which are incorporated herein by reference. The test described therein is hereinafter referred to as the Sealey, and Laragh PRA test. Tests for measuring PRA which may be developed or adopted in the future and which have substantially equal or greater sensitivity and accuracy also may be used in the Laragh Method.

There are no special dietary or activity requirements for performing the test. The patient should not be supine and should have blood drawn in the normal clinical setting. Knowledge of any use of antihypertensive or cardiovascular drugs is important.

To be properly performed, the PRA test, should achieve maximum sensitivity because this enables a full exploration and definition of subnormal plasma renin levels that are encountered in about 30 percent or more hypertensive patients. Maximum sensitivity is achieved by the enzyme kinetic assay which allows the prolonged (18 hour) incubation of the plasma sample which generates thousands of copies of angiotensin that can then be detected by radioimmunoassay.

Thus, by full definition of the subnormal range one may accurately discriminate low renin patients from medium to high renin patients and thereby precisely define who is at risk of premature heart attack and who is not. The test discriminates those hypertensive patients who have a renin factor (PRA$\geq$0.65 to 10 ng/ml/hr or higher) from those who have instead a sodium volume factor in whom the lowness of the PRA values (<0.65) is a direct measure of the sodium volume factor. In short, those renin assays which cannot precisely identify low values cannot quantify the extent of the volume and/or the renin factors in hypertensive patients. Several simple and direct immunioradiometric methods for renin measurements have been published, all of which have a major deficiency in sensitivity. Another artifact in renin assays is caused by chilling blood and plasma samples which has been shown to cryoactivate prorenin to renin (Sealey 1976) leading to artificially high plasma renin values of tenfold or more an error which is especially likely to occur in diabetic and in low-renin hypertensive patients.

Using the enzyme kinetic method described above, 30% of untreated ambulatory hypertensive patients (BP>140/95) exhibit low values PRA<0.65. Sixty percent have medium values 0.65 to 3.0 and 10% have high values>3.0.

Most normal subjects with their lower pressures exhibit somewhat higher renin values (1.0–3.0 ng/mg/hr) than do hypertensives. This is a consequence of the raised blood pressure in the renal arteries of the hypertensives acting to suppress their kidney renin release. Because of this effect, any plasma renin in the blood should be considered to be abnormal in a hypertensive person, because whenever blood pressure is raised in a normal person by salt feeding or by neosynephrine injection, plasma renin values will promptly fall to zero.

We have found that patients with curable renovascular hypertension consistently exhibit PRA>1.5 ng/ml/hr and patients with curable adenomatous primary aldesteronism consistently exhibit very low values, i.e., PRA<0.65ng/ml/hr.

Initiating Treatment Using the Laragh Method

The two general classes of antihypertensive drugs utilized by the Laragh Method, the anti-volume V drugs and the anti-renin R drugs have been discussed above. With this drug classification in hand, the Laragh Method also divides all hypertensive patients into two major groups according to their plasma renin level: (1) those who are progressively more likely to have a renin-angiotensin pressor and vasculotoxic factor (PRA≧0.65 ng/ml/hr) and (2) low renin patients, i.e., those who do not have a plasma renin factor (PRA<0.65 ng/ml/hr) and who have instead, a predominant sodium-volume factor sustaining the hypertension.

A preferred use of the PRA test to guide initial drug treatment is illustrated below in Table V. If the PRA is not known, it is advisable to start the patient with an R drug because the great specificity of these drugs (especially the ARB's) provides powerful diagnostic information implicating plasma renin in causation if the blood pressure crashes and vice versa. No response to an R drug implicates a sodium volume mechanism instead.

TABLE 5

Using Plasma Renin Activity (PRA) to Guide Initial Drug Treatment of Untreated Hypertensive Patients

| PRA Known | PRA Unknown |
|---|---|
| PRA < 0.65 Always Start with V drug PRA ≥ 0.65 Start with R drug | Always Start with an R drug |

Patients with PRA≧0.65 ng/m/hr normally may not have exclusively renin-dependent hypertension and may have a volume component to their hypertension. Likewise, low renin patients may have a small renin component to their blood pressure. Just as in normotensive people, the sodium volume factor and the plasma renin levels are always interacting in varying proportions to support the observed blood pressure. Thus, the closer the renin level is to 0.65 ng/ml/hr, the more likely that some degree of both the renin and sodium-volume components are present. However, because excess plasma renin levels are much more highly associated with cardiovascular injury to heart, brain and kidney vessels than is excess body sodium-volume, in designing the treatment strategy, the Laragh Method treats the renin factor first and then only if the response is poor, does the Laragh Method provide for treatment of the sodium-volume factor instead.

In implementing the Laragh Method, the blood pressure of the patient may be measured by any one of several methods known to a person of skill in the art or preferred by an individual physician or health care worker. Target blood pressures, and what constitutes controlled blood pressure or adequately controlled blood pressure, also maybe identified by one of several values or measurements known to a person of skill in the art or preferred by an individual physician or health care worker. Regardless of the actual blood pressure measurement used or the target or a desired blood pressure selected, the Laragh Method can be used to lower and help control patients' blood pressures.

Certain other tests and procedures mentioned herein (Captopril test, renal vein sampling, renal angiogram, adrenal CT scan, adrenal vein sampling, 24 hr urine aldosterone, hypokalemia evaluation, renal angioplasty, surgical revascularization, unilateral adrenalectomy, etc.), are well known to a person of skill in the art and recognized tests and procedures and their equivalents may be used. Any actual values, measurements or observations obtained by these tests are less important than what the values indicate.

The Laragh Method may indicate that a certain drug should be prescribed and then the patient's blood pressure measured to determine whether the drug has been effective. This determination of the effectiveness of the drug by measuring the blood pressure should be done after enough time has elapsed for the drug to be given an opportunity to act. This time may vary according to the drug and depend on a number of factors such as how long the drug takes to be effective. Thus, follow-up visits to an office, hospital or clinic and the measurement of blood pressure should be scheduled to take into account the drug being prescribed and how long it takes to act.

In exemplary embodiments of the Laragh Method, drugs which are prescribed may be administered by a physician or health care provider under the direction of a physician, including, but not limited to, one or more physician's assistant, nurse, technician, or pharmacist. As used herein, patients may also administer the drugs to themselves. "Administering" may include, but is not limited to, for example, to prescribe, to provide, to recommend, or to suggest through oral or written communication.

Protocol I: Using Plasma Renin Activity (PRA) to Guide Treatment of New or Untreated Hypertensive Patient FIG. 4 and Table 6 below outline an exemplary embodiment of the Laragh Method for the new or untreated patient. In this exemplary embodiment of the Laragh Method, the evaluation and treatment comprises a series of visits by the patient. In Visit 1 blood pressure (BP) is measured, and blood is drawn to determine plasma renin activity (PRA). In Visit 2, if the PRA is less than 0.65, the patient is placed in the volume dependent (V) hypertension category. If the PRA is greater than or equal to 0.65 ng/ml/hr, the patient is placed in the vasoconstriction-dependent (R) hypertension category.

A patient in the V category at Visit 2 may start on a low dose V drug. Such a patient in Visit 3 will have his or her BP tested again. If BP is within acceptable levels, subsequent visits will involve routine follow-up. If BP is not controlled, the dose of the V drug is increased. At Visit 4 if BP is controlled, subsequent visits will involve routine follow-up. If BP is not controlled, an R drug is added to the treatment regimen. At Visit 5, if BP is controlled, subsequent visits will involve routine follow-up. If BP is not controlled, the R drug dosage is increased and blood is drawn to check PRA levels. At Visit 6, if BP is controlled, then subsequent visits will involve routine follow-up. If BP is not controlled, the change in the treatment regimen depends on the PRA level. If the PRA level is below 0.65 ng/ml/hr, the R drug is discontinued and a second V drug is added. If the PRA level is between 0.65 and 6.5 ng/ml/hr, a second R drug is added. If the PRA level is above 6.5, the V drug is discontinued and a second R drug is added.

Figure 4:
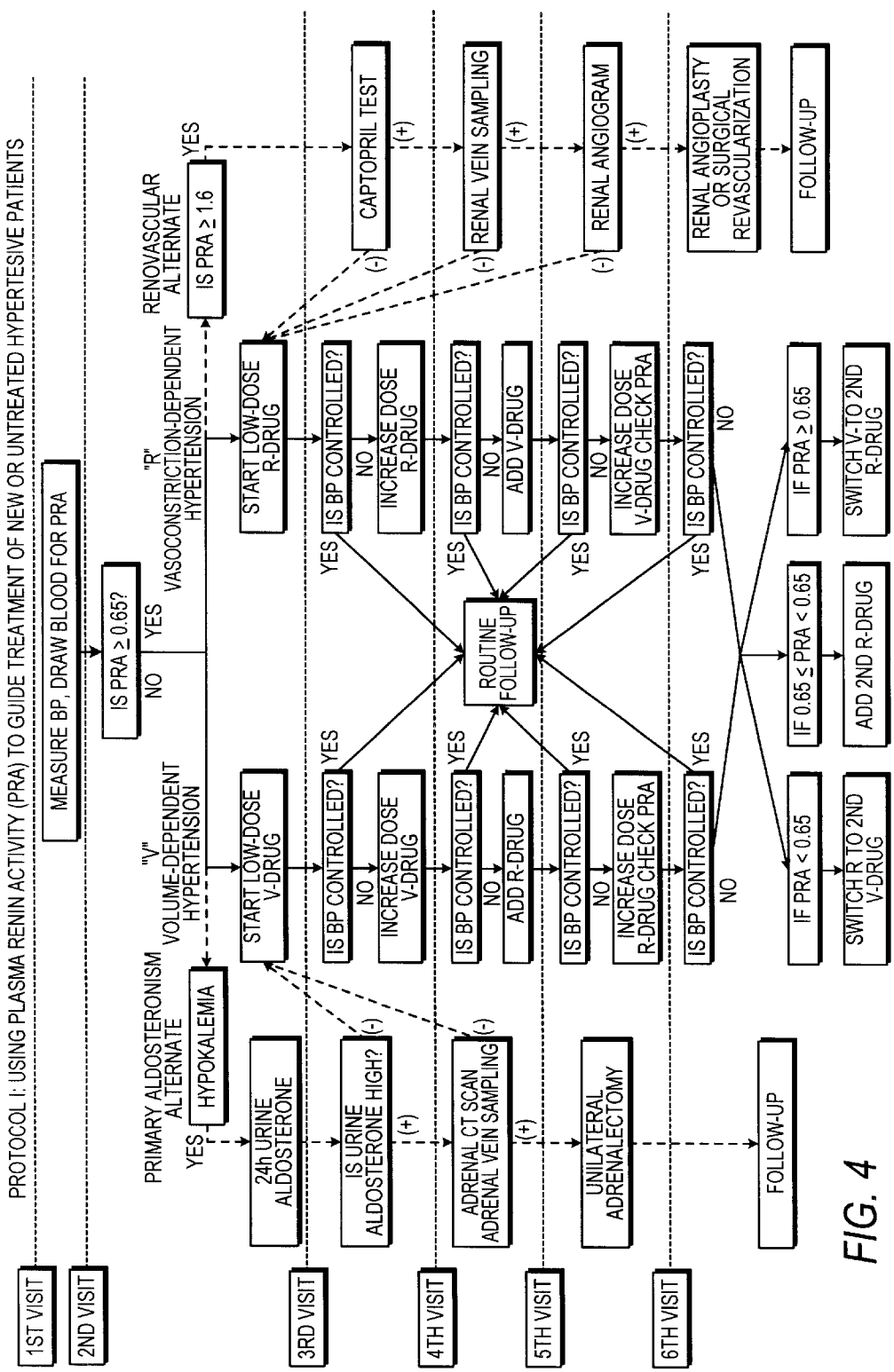
FIG. 4 is a flow chart depicting an exemplary embodiment of the Laragh Method for the evaluation and treatment of previously untreated hypertensive patients.

As shown in FIG. 4, an alternate treatment protocol for a hypokalemic patient in the V category is to test for the presence of surgically-curable primary aldosteronism at Visit 2, rather than starting on a low dose V drug. If the patient is hypokalemic, a 24 hour urine aldosterone test is performed. At Visit 3 if the 24 hour urine aldosterone is normal, the patient should start on a low dose V drug as described above for Visit 2. The steps as described above for Visits 3–6 are then followed. If the 24 hour urine aldosterone is high at Visit 3, Visit 4 should comprise an adrenal CT scan and/or an adrenal vein sampling. If the results of the tests conducted in Visit 4 are negative, the patient should start on a low dose V drug as described above for Visit 2. The steps as described above for Visits 3–6 are then followed. If the results of the tests conducted in Visit 4 are not negative, Visit 5 may comprise a unilateral adrenalectomy, followed by post-operative follow-up in Visit 6 and subsequent routine follow-up thereafter.

Conversely, if the patient has been classified as an R category hypertensive; at Visit 2 this patient may start on a low dose R drug. This patient in Visit 3 will have his or her BP tested again. If BP is within acceptable levels, subsequent visits will involve routine follow-up. If BP is not controlled, the dose of the R drug is increased. At Visit 4 if BP is controlled, subsequent visits will involve routine follow-up. If BP is not controlled, a V drug is added to the treatment regimen. At Visit 5 if BP is controlled, subsequent visits will involve routine follow-up. If BP is not controlled, the V drug dosage is increased and blood is drawn to check PRA levels. At Visit 6, if BP is controlled, then subsequent visits will involve routine follow-up. If BP is not controlled, the change in the treatment regimen is dependent on the PRA level. If the PRA level is below 0.65, the R drug is discontinued and a second V drug is added. If the PRA level is between 0.65 and 6.5, a second R drug is added. If the PRA level is above 6.5, the V drug is discontinued and a second R drug is added.

As shown in FIG. 4, an alternate treatment protocol for a patient in the R category with PRA>1.6 ng/ml/hr is to test for a primary renovascular hypertension as an explanation for the patient's hypertension at Visit 2, rather than starting on a low dose R drug. If the PRA level is above 1.6, Visit 3 may comprise a captopril test. If the captopril test is negative, the patient should start on a low dose R drug as described above for Visit 2. The steps as described above for Visits 3–6 are then followed. If the captopril test is positive at Visit 3, Visit 4 may comprise renal vein renin sampling. If the results of the renal vein renin sampling conducted in Visit 4 are negative, the patient should start on a low dose R drug as described above for Visit 2. The steps as described above for Visits 3–6 are then followed. If the renal vein renin sampling conducted in Visit 4 is not negative, Visit 5 may comprise a renal angiogram. If the results of the renal angiogram conducted in Visit 5 are negative, the patient should start on a low dose R drug as described above for Visit 2. The steps as described above for Visits 3–6 are then followed. If the results of the renal angiogram are not negative, Visit 6 may comprise renal angioplasty or surgical revascularization, followed by post-operative follow-up and subsequent routine follow-up thereafter.

TABLE 6

EXEMPLARY PROTOCOL FOR NEW OR UNTREATED HYPERTENSIVE PATIENTS BASED ON PLASMA RENIN ACTIVITY (PRA) TESTING

| | PRA test | PRA result | Current drug regimen | % Patients Corrected | Drug changes |
|---|---|---|---|---|---|
| 1st visit | X | | None | 0% | None, return 1–3 weeks |
| 2nd visit | | X | None | 0% | PRA <0.65, start V drug<br>PRA ≧0.65, start R Drug |
| 3rd visit | | | On low dose V or R drug | 25% | Increase dose |
| 4th visit | | | On max dose V or R drug | 50% | Add V to R or R to V drugs |
| 5th visit | X | | On V + R drug | 75% | Increase dose of 2nd drug |
| 6th visit | | X | On max dose V + R drug | 90% | PRA <0.65, switch R to 2nd V drug<br>PRA 0.65 to 6.5, add 2nd R drug<br>PRA ≧6.5, switch V to 2nd R drug |

FIG. 4 and Table 6 above outline an exemplary embodiment of the Laragh Method for the new or untreated patient by setting forth a schedule of PRA tests, an analysis of the results of the tests, and the implications for changing drugs based on the results of the tests during a sequence of office visits. As indicated in FIG. 4 and in Table 6, the untreated hypertensive patient with a plasma renin (PRA) level at or above 0.65 ng/ml/hr is likely to have a renin-angiotensin component to the hypertension that is in proportion to the height of the renin value. In contrast, patients with suppressed PRA values (<0.65 ng/ml/hr) are more likely (based on the lowness of the PRA value) to have hypertension that is caused by excessive sodium-volume retention. In them, the lowness of the renin factor indicates the degree of sodium-volume excess. Because excess renin is more vasculotoxic than is excess volume in hypertensive patients, and because renin-angiotensin is a more common cause of essential hypertension than sodium-volume, all untreated patients with a PRA level at or above 0.65 ng/ml/hr should be treated initially with a drug that blocks the renin-angiotensin system because if that treatment is successful, it is more likely to prevent cardiac and vascular damage over the long term. For reasons already discussed, patients with PRA values<0.65 ng/ml/hr should be initially treated with a V drug.

Figure 5:
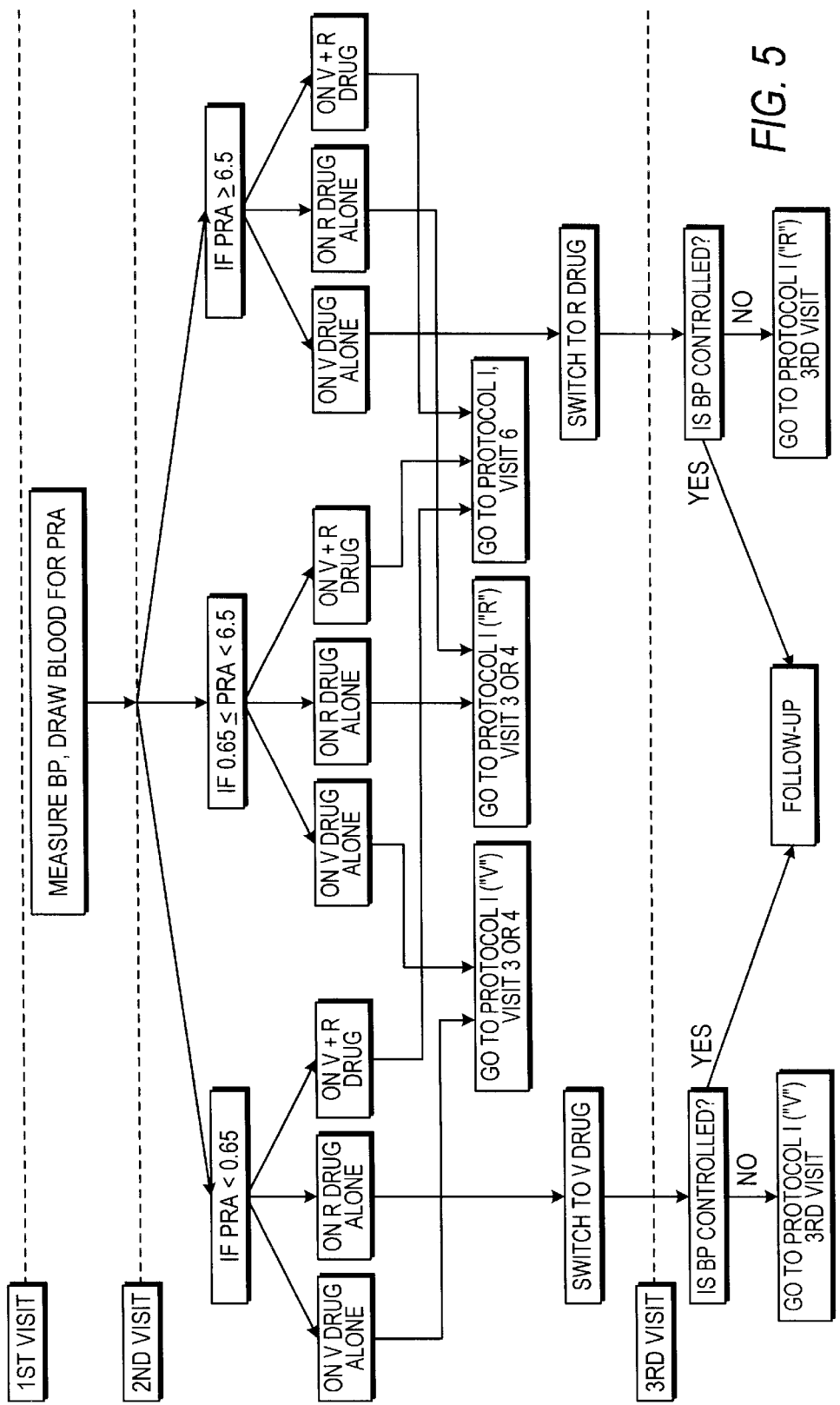
FIG. 5 is a flow chart depicting an alternate exemplary embodiment of the Laragh Method used for the evaluation and treatment of unsuccessfully treated hypertensive patients.

Protocol II: Using Plasma Renin Activity (PRA) to Guide Treatment of Unsuccessfully Treated Patients As indicated by FIG. 5 and Table 7 below, another exemplary embodiment of the Laragh Method is quite useful for determining which drug or drugs to select for the previously unsuccessfully treated hypertensive patient. The Laragh Method can be used for (a) patients on one or more V drugs, (b) patients on one or more R drugs, or (c) patients receiving one or more R and V drugs. As was the case for Protocol I, an exemplary embodiment of Protocol II may comprise a series of steps or visits.

Visit 1 (as in Protocol I) may comprise measuring BP and drawing blood to test PRA levels. The appropriate action to take during Visit 2 is dependent on the PRA level. If the PRA level is below 0.65 ng/ml/hr and the patient is on a V drug alone, the patient may be treated consistent with the V side of Protocol I (FIG. 4), Visit 3 or 4. If the PRA level is below 0.65 ng/ml/hr and the patient is on an R drug alone, the R drug may be discontinued and treatment with a V drug initiated. This patient in Visit 3 will have his or her BP checked. If BP is controlled, subsequent visits will comprise routine follow-up. If BP is not controlled, the patient may be treated consistent with the V side of Protocol I, Visit 3. If the PRA level is below 0.65 and the patient is on both a V and R drug, the patient should be treated consistent with Protocol 1, Visit 6.

If a patient in Protocol II, Visit 2 has a PRA level between 0.65 and 6.5 and is on a V drug alone, such a patient may be treated as if on the V side of Protocol I, Visit 3 or 4. If a patient in Protocol II, Visit 2 has a PRA level between 0.65 and 6.5 and is on an R drug alone, such a patient may be treated as if on the R side of Protocol I, Visit 3 or 4. If a patient in Protocol II, Visit 2 has a PRA level between 0.65 and 6.5 and is on both a V drug and an R drug, such a patient may be treated as if in Protocol I, Visit 6.

If the PRA level is above 6.5 and the patient is on a V drug alone, the V drug may be discontinued and treatment with an R drug initiated. This patient in Visit 3 will have his or her BP checked. If BP is controlled, subsequent visits will comprise routine follow-up. If BP is not controlled, the patient may be treated consistent with the R side of Protocol I, Visit 3. If the PRA level is above 6.5 and the patient is on an R drug alone, the patient may, be treated consistent with the R side of Protocol I, Visit 3 or 4. If the PRA level is above 6.5 and the patient is on both a V and R drug, the patient should be treated consistent with Protocol 1, Visit 6.

TABLE 7

EXEMPLARY PROTOCOL FOR UNSUCCESSFULLY TREATED PATIENTS

| | PRA test | PRA result | Current drug regimen | Drug changes based on treatment PRA |
|---|---|---|---|---|
| Protocol IIa (on one or more anti-volume drugs) | | | | |
| 1st visit | X | | On Maximum V drug | Return in 1 week |
| 2nd visit | | X | On Maximum V drug | PRA <0.65, add 2nd V drug |
| | | | | PRA 0.65 to 6.5, add R drug |
| | | | | PRA ≧6.5, switch to R drug* |
| Protocol IIb (on one or more anti-renin drugs) | | | | |
| 1st visit | X | | On Maximum R drug | Return in 1 week |
| 2nd visit | | X | On Maximum R drug | PRA <0.65, switch to V drug |
| | | | | PRA 0.65 to 6.5, add V drug |
| | | | | PRA ≧6.5, add 2nd R drug* |
| Protocol IIc (on one or more anti-renin and anti-volume drugs) | | | | |
| 1st visit | X | | On V drug + R drug | Return in 1 week |
| 2nd visit | | X | On V drug + R drug | PRA <0.65, switch R to 2nd V drug |
| | | | | PRA 0.65 to 6.5, add 2nd R drug |
| | | | | PRA ≧6.5, switch V to 2nd R drug* |

*The higher the PRA level, the more likely that a 2nd R drug may be needed

Protocol IIA: For Unresponsive Hypertensive Patients Already Taking V Drug(s)

In more general terms, as shown in FIG. 5 and Table 7, the Laragh Method provides that a patient still in the titration phase of a single V drug should have the dose of the drug increased to a maximum level as long as the PRA remains below 0.65 ng/ml/hr. In such a patient the sodium-volume factor is still operative and contributing to the hypertensive state. Since a renin factor is unlikely to be present in any patient with a low renin level, a patient on any V drug who remains hypertensive with a PRA level less than 0.65 ng/ml/hr is unlikely to respond to any R drug. Therefore, if a full dose of a V drug has already been tested, and assuming good compliance, a V drug with a different mechanism of action should be added. Thus, an exemplary embodiment of the Laragh Method provides that a diuretic can be added to a SARA or vice versa, and then an alpha blocker or CCB, could be added to a diuretic or SARA.

Irrespective of whether the hypertensive patient is untreated or treated with a V drug, the higher the PRA level the more likely the patient is to have a renin component to the hypertension. If such an unresponsive patient is already on a full dose of V drug, the Laragh Method provides that an R drug should be added if the patient's PRA level is equal to or greater than 0.65 ng/ml/hr. However, if the patient's PRA is equal to or greater than 6.5, the Laragh Method directs that diuretics should be stopped and an R drug started because such high renin levels indicate some dehydration.

Protocol IIB: For Unresponsive Hypertensive Patients Already Taking R Drug (s)

Since a renin factor is unlikely to be present in any treated patient with a low renin level (except one treated with a beta blocker), an exemplary embodiment of the Laragh Method provides that any patient on a full dose of a CEI or ARB with a PRA level less than 0.65 ng/ml/hr who remains hypertensive should be switched a V drug. For patients who are on less than a full R drug dose and have PRA levels equal to or greater than 0.65, it is worthwhile to first test an increase in dose and/or add another R drug before returning.to the R side of Protocol I visit 4.

According to an exemplary embodiment of the Laragh Method, a patient with a PRA equal to or greater than 0.65 ng/ml/hr who is unsuccessfully treated with a full dose of any R drug (CEI, ARB or beta blocker) should then have a V drug added as long as PRA is less than 6.5 ng/ml/hr. At or above this level the patient should be treated with a second R drug because, although the three classes of R drugs all block the renin-angiotensin system, they have different sites of action and may be additive for increasing inhibition of the renin system. Thus, at the recommended maximal therapeutic doses, neither CEIs nor ARBs are complete blockers of the renin system and a reactive rise in renin secretion will sometimes overcome or attenuate the effectiveness of these agents in blocking the renin system. Moreover, beta blockers act to prevent the beta adrenergic drive to renin release, and may sometimes be needed to amplify the anti-renin blockade achieved by a CEI or ARB or both, each of which blocks the renin system at a different points.

Protocol IIC: For Unresponsive Hypertensive Patients Already Taking One or More R and V Drugs According to an exemplary embodiment of the Laragh Method as indicated in FIG. 5 and Table 7, a PRA test on the first visit is extremely helpful in this situation because it can reveal which mechanism predominates. Thus, PRA values less than 0.65 clearly indicate a sodium-volume excess is present and the patient should be treated as having a primary volume problem. The R drug should be stopped and a second V drug added. Conversely, if the PRA is between 0.65 and 6.5, the anti-renin limb of treatment needs to be strengthened by the addition of a second R drug. Above 6.5 ng/ml/hr, the V drug should be stopped because it may be causing excessive reactive renin secretion. A second R drug can be added, if necessary.

Thus, to summarize, the strategy dictated by an exemplary embodiment of the Laragh Method is to strengthen the V limb for PRA less than 0.65 and stop the anti-renin drugs. When the PRA is between 6.5 and 0.65 an R drug should be added. However, for those patients with PRAs equal to or greater than 6.5, the diuretic therapy should be stopped when the R limb is strengthened because such high renin values are usually associated with sodium-volume depletion and overly reactive renin secretion.

Figure 6:
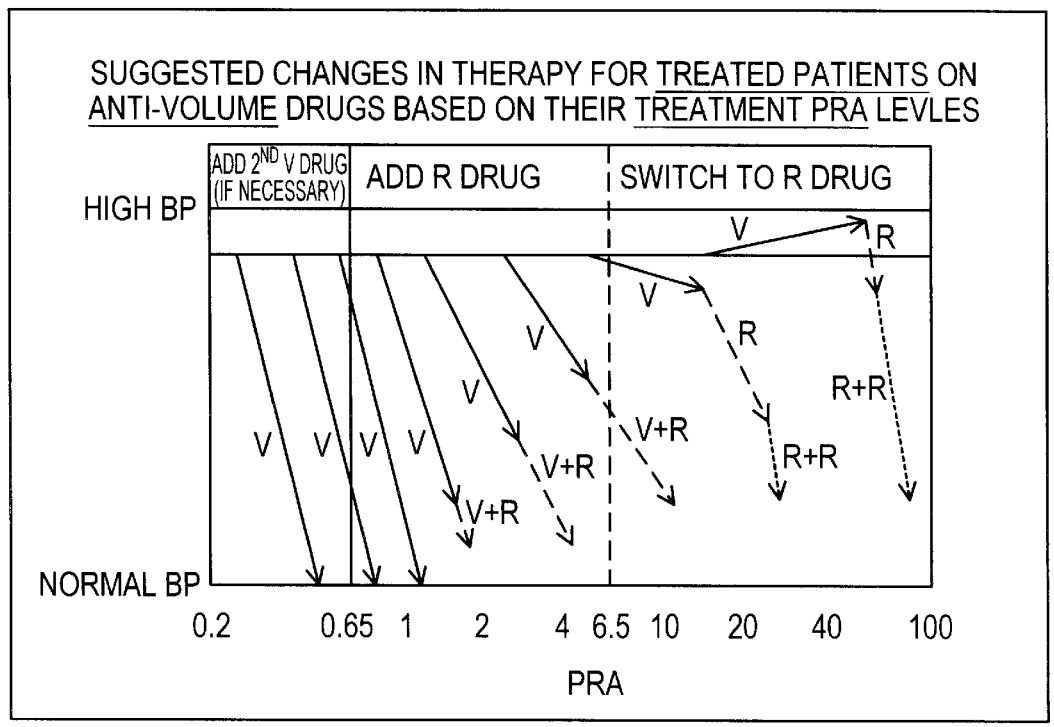
FIG. 6 illustrates suggested changes in therapy called for by the Laragh Method in unsuccessfully treated patients on anti-volume drugs based on their treatment plasma renin levels.

Suggested Changes in Therapy for Treated Patients on V Drugs Based on Their Treatment PRA Levels The same patients illustrated in FIG. 2 are again illustrated in FIG. 6 but with suggested changes in treatment for those whose BP was not optimally corrected. The solid lines (also shown in FIG. 2) and the dashed lines indicate the changes in PRA and BP induced by the first and second changes in treatment respectively.

Most patients with treated PRA levels less than 0.65 ng/ml/hr who are taking a diuretic are likely to be successfully treated. If further reduction in BP is necessary a second V drug should be added.

Patients with PRA levels on a V drug between 0.65 and 6.5 ng/ml/hr may have both volume and vasoconstrictor components to their blood pressure and are likely to respond best to the addition of an R drug to the V drug.

Patients with PRA levels above 6.5 ng/ml/hr on V drug(s) may have had a large reactive rise in PRA with the diuretic. If an R drug is added they are likely to have an even greater rise in PRA levels which could overwhelm the effects of anti-renin system blockade. In them the V drug should be stopped when the R drug is started. It is possible that such patients may eventually need a second R drug to completely control their BP (dotted arrow). Renovascular hypertension is common in patients who exhibit highly reactive renin levels.

Suggested Changes in Therapy for Treated Patients on R Drugs Based on Their Treatment PRA Levels.

Figure 7:
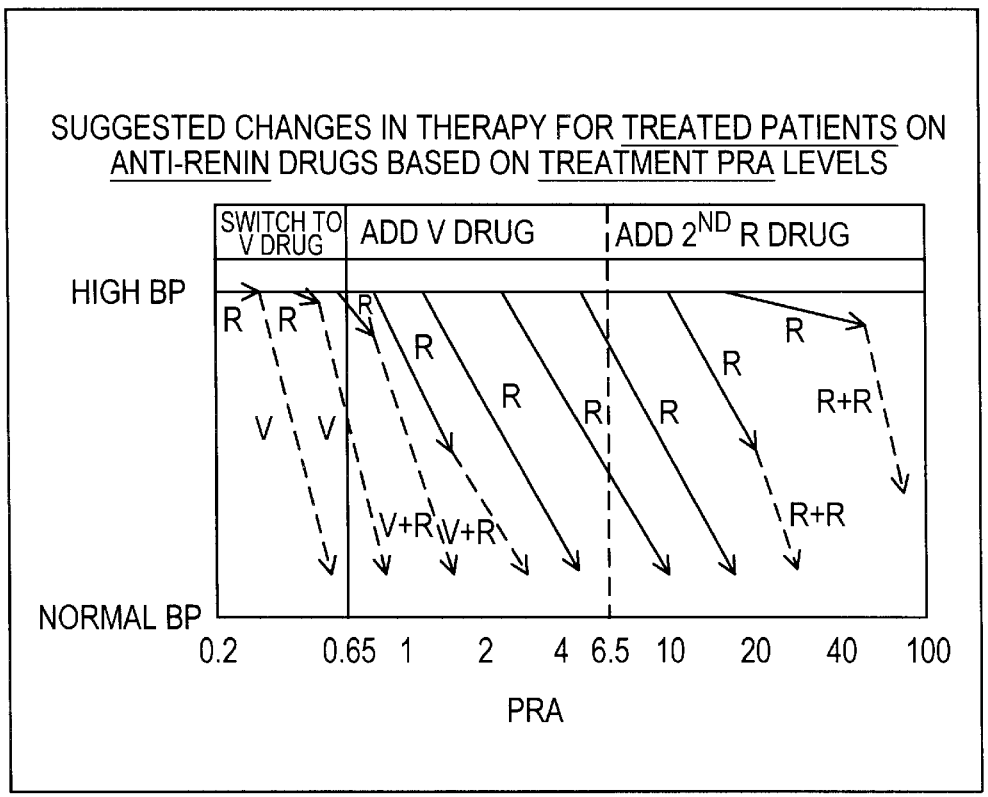
FIG. 7 illustrates suggested changes in therapy called for by the Laragh Method in unsuccessfully treated patients on anti-renin drugs based on treatment plasma renin levels.
Figure 8:
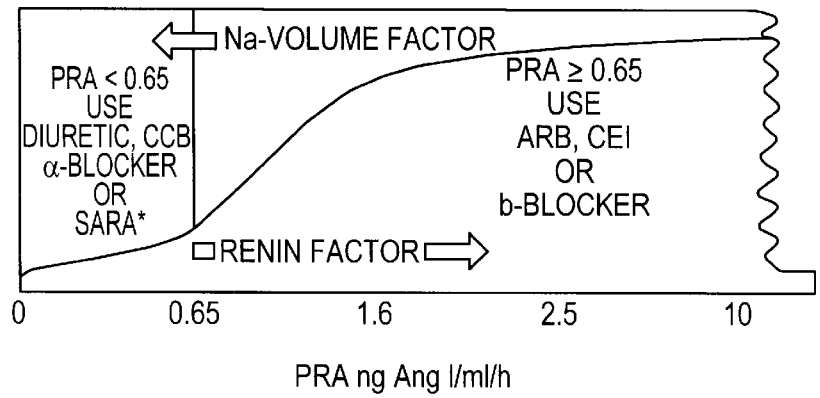
FIG. 8 illustrates the use of plasma renin levels to select drug treatments to reduce the cardiovascular risks associated with excess plasma angiotensin levels.

The same hypothetical patients illustrated in FIG. 3 are again illustrated in FIG. 7 but with suggested changes in treatment for those whose BP was not optimally corrected. The solid line indicates the changes in PRA and BP caused by the first line of therapy (also illustrated in FIG. 3). The dashed lines indicate the changes in PRA and BP induced by the suggested change in treatment. The solid arrow head indicates the PRA (and BP) values that were used to determine further treatment.

Unsuccessfully treated patients with treatment PRA levels less than 0.65 ng/ml/hr should be switched to a V drug. The low treatment PRA level indicates that the patient was unresponsive to the R drug.

Unsuccessfully treated patients with treatment PRA levels between 0.65 and 6.5 ng/ml/hr are likely to have both volume and vasoconstrictor components to their blood pressure and are likely to respond best to the combination of a Y drug and an R drug.

Unsuccessfully treated patients with treatment PRA levels above 6.5 ng/ml/hr may have had such a reactive rise in PRA with the R drug that they overwhelmed the anti-renin system blockade. In them the addition of a V drug is not indicated because it could induce an even greater rise in PRA. That is why the addition of a second R drug is indicated here.

The Laragh Method May Be Used to Evaluate and Treat Hypertensive Crises

The Laragh Method as applied to the evaluation and treatment of hypertensive crises is superior to traditional strategies which focus entirely on blood pressure correction per se, perhaps on the assumption that this is the only relevant traditional target. Traditional strategies, however, are faulty because they fail to promptly identify the causal mechanisms, while embodiments of the present invention allow prompt identification of causal mechanisms by immediately exploiting plasma renin testing and the blood pressure responses to specific pharmacologic probes to target causal mechanisms for more specific corrective drug treatments.

Thus, in contrast to the Laragh Method, the traditional recommended approaches have relied heavily on I.V. nitroprusside or I.V. or oral calcium channel blockers, either of which are seductive because they will in fact at least partially reduce the high blood pressure immediately. But at the same time, whenever there is no mechanistic diagnosis, precious time is lost which could have been used to gain vital diagnostic information about the basic causal mechanisms involving renin-angiotensin and sodium-volume mechanisms. Moreover, in the case of nitroprusside, serious risks from the labor-intensive procedure itself and the associated higher costs, contribute negatively to the overall goal of promptly determining causation. In short, since renin-angiotensin excess is the most common single cause of hypertensive crises and of attendant severe vascular injury to heart, brain and kidney, the primary use of either nitroprusside or CCB's in fact often proves to be a sojourn of lost time during which hypotension may be transiently achieved but without establishing a definitive diagnosis. This leaves the physician unprepared to make the inevitable switch to the correct drug class for treating the individual.

The spectrum of disorders associated with high blood pressure ranges from chronic mild uncomplicated hypertension to more severe and complicated forms of hypertensive syndromes, the most severe of which are defined as either hypertensive emergencies or hypertensive urgencies. While these more urgent and severe hypertensive states may vary widely in their presentations, all involve an acceleration of the same pathophysiologic abnormalities (the renin vasoconstrictor and the sodium-volume pressor mechanisms) that are involved in sustaining the milder or more slowly progressing forms of chronic hypertension.

The basic strategies and procedures embodied in the Laragh Method for achieving a mechanistic diagnosis and selecting the correct drug treatment for the individual patient with a hypertensive crisis remain and are in principle like those applied to evaluation of milder forms of hypertension. They are modified to achieve a mechanistic diagnosis and the correct drug treatment in the most rapid, "fast-forward" mode possible. Thus, just as in milder hypertensive states the Laragh Method provides that the most effective approach to emergency or urgency situations involves the assessment of the presence and degree of the two pathways that are sustaining the hypertensive condition, i.e., the plasma renin-angiotensin vasoconstrictor factor and the sodium-volume factor.

The JNC (Joint National Commission on Detection, Evaluation, and Treatment of High Blood Pressure) classifies hypertensive crises as either hypertensive "emergencies" or "urgencies". Table 8 below lists several types of hypertensive crises categorized as either hypertensive emergencies or hypertensive urgencies. Hypertensive emergencies are those situations that require immediate blood pressure reduction, (not necessarily to normal) in order to prevent or reduce the risk of potentially fatal target organ damage, from stroke, heart attack, hearts failure or kidney failure. Hypertensive urgencies are those situations in which it is desirable to reduce BP within a few hours. Examples include upper levels of stage 3 hypertension, hypertension with optic disc edema, progressive target organ complications, and severe perioperative hypertension.

TABLE 8

HYPERTENSIVE EMERGENCIES

Malignant Hypertension
Other High Renin States:

Renal Ischemic Vascular Disease
Renal Vasculitis (scleroderma, periarteritis, lupus)
Renal Trauma
Renin-secreting tumors
Adrenergic crises: pheochromocytoma, cocaine abuse, clonidine withdrawal
Dissecting aortic aneurysm
Hypertensive encephalopathy
Hypertension with stroke or impending stroke (TIA)
Hypertension with pulmonary edema
Hypertension with acute myocardial infarction
HYPERTENSIVE URGENCIES Hypertension with unstable angina
Accelerating or severe hypertension
Perioperative hypertension
Cocaine abuse
Clonidine withdrawal
Sodium-volume overload forms:

Acute renal failure
Acute glomerulonephritis
Low urinary tract obstruction
Primary aldosteronism
Low renin essential hypertension with pseudopapilledema
Preeclampsia Table 9 below lists most of the recognized hypertensive emergencies or urgencies and includes what is already known about renin-angiotensin or sodium-volume involvement in their causation or maintenance. It also includes those conditions associated with excessive neuro-adrenal hormonal activity, related either to excessive central or adrenal medullary-induced release of catecholamines, either noradrenalin, adrenalin or both. A large component of catecholamine pressor action can involve constriction of kidneys vessels leading to excess kidney renin-angiotensin release.

TABLE 9

THE RENIN ANGIOTENSIN AND/OR SODIUM → VOLUME
MEDIATION OF HYPERTENSIVE EMERGENCIES OR URGENCIES:

A. Dry Vasoconstrictor-High Renin Forms (PRA ≧0.65) have signs of vascular injury to heart, brain and kidneys.
   1. Malignant Hypertension
   2. Unilateral renovascular hypertension
   3. High renin essential hypertension
   4. Renal Trauma or infarction
   5. Renin-secreting tumors
   6. Renal vasculitis (periarteritis, scleroderma, lupus)
   7. Adrenergic Crises: pheochromocytoma, cocaine abuse, clonidine withdrawal
   8. Cocaine abuse, clonidine withdrawal
B. Wet-Sodium-Volume Mediated V Forms of acute hypertension (Plasma Renin <0.65 to very low).
   1. Acute renal failure
   2. Acute glomerulonephritis
   3. Lower urinary tract obstruction
   4. Low renin essential hypertension
   5. Primary hyperaldosteronism
   6. Eclampsia (PRA falls from 6–10 range of normal pregnancy to 1–2 ng/ml/hr)
C. Mixed Renin-Sodium Volume Forms of Hypertension. The Degree of ≧0.65 or <0.65 indicates a predominant renin or volume factor.
   1. Bilateral renal artery stenosis the high blood pressure of these conditions can
   2. Coarctation of the aorta TABLE 9-continued THE RENIN ANGIOTENSIN AND/OR SODIUM → VOLUME
MEDIATION OF HYPERTENSIVE EMERGENCIES OR URGENCIES:

*The high blood pressure of these conditions can normally be volume dependent, but after sodium depletion it is sustained instead by plasma renin increase.
D. Other probable* medium to high renin states: PRA ≧0.65
   1. Hypertensive encephalopathy
   2. Hypertension with cerebral hemorrhage
   3. Hypertension with (impending) stroke
   4. Hypertension with pulmonary edema
   5. Hypertension with acute myocardial infarction or with unstable angina
   6. Dissecting aortic aneurysm
   7. Perioperative hypertension (renin involvement reactive to noradrenalin or adrenalin release).
*These are hypertensive emergencies or urgencies for which no systematic information on plasma renin or sodium-volume states is yet available. Nonetheless, the Laragh Method's use of renin testing in conjunction with the blood pressure response to an R or V drug can still faithfully reveal and target for treatment, the presence and/or degree of the renin or the sodium volume factor in sustaining the hypertension.

The Laragh Method provides a protocol for rapid evaluation and treatment of hypertensive emergencies and urgencies and include, for example, those shown in Tables 8 and 9. In an exemplary embodiment, for accelerating the processes to treat hypertensive crises, the Laragh Method provides that the process begins by obtaining entry plasma renin activity (PRA) and plasma catecholamine measurements along with testing blood for routine parameters. (See Table 10 below which sets forth an exemplary embodiment of this systematic approach.) This is followed immediately thereafter by systematic testing of the blood pressure responses at 30 to 60 minutes intervals, first after administering an anti-renin R drug, most preferably either I.V. enalaprilat or 50 mg captopril orally. As in the milder forms of hypertension, a large response implicates plasma renin-angiotensin levels in causation while no response suggests a sodium volume causation instead.

TABLE 10

Procedures For The Rapid Mechanistic Approach To Diagnosis And Treatment Of Hypertensive Emergencies Or Urgencies: The Laragh Vasoconstriction (Renin Angiotensin-Sodium-Volume Analysis In Fast Forward 1. Baseline Laboratory Profile:
      CBC
      Plasma renin activity
      Plasma catecholamines: norepinephrine, epinephrine
      Electrolytes, urea, creatinine, uric acid, glucose
      ECG and Echo
2. Perform a rapid vasoconstriction (renin-angiotensin) (sodium-volume) analysis i.e.: Diagnosisexjuvantibus: the blood pressure response to the drug informs the diagnosis. Use I.V. or rapidly acting oral drugs in series, every 30–45 minutes to determine BP response and inform the diagnosis.
   (1) Oral captopril or I.V. enalaprilat to identify the presence or absence of the renin factor.
   (2) I.V. Phentolamine plus esmolol or labetalol I.V. to quantify the neural factor and to rule out pheochromocytoma, cocaine abuse, or clonidine withdrawal.
   (3) I.V. furosemide to quantify the volume factor.
3. Continue therapy with the effective agent(s) from the above. Add or substitute non-specific vasodilators, BUT only if needed. Eg: I.V. nicardipine or verapamil, I.V. nitroprusside, nitroglycerine, hydralazine or diazoxide.
4. In bleeding states, e.g.: cerebral or aortic dissection, or in acute myocardial infarction use instead or first agents that reduce cardiac work and vascular wall stress (i.e. beta blockers).

TABLE 10-continued

Procedures For The Rapid Mechanistic Approach To Diagnosis And Treatment Of Hypertensive Emergencies Or Urgencies: The Laragh Vasoconstriction (Renin Angiotensin-Sodium-Volume Analysis In Fast Forward 5. As blood pressure falls with renin system blockade concurrent sodium volume repletion may be required.
6. The response or lack of response to the specific anti-renin (R) or anti-sodium (V) drugs taken together with follow-up plasma renin level also guide follow-up drug therapy.

The second pharmacologic testing step is designed to quickly rule in or out, whenever clinically appropriate, catecholamine (i.e., adrenalin or noradrenalin) related hypertension from, for example, an adrenal tumor, (e.g., a pheochrornocytoma), or from cocaine abuse or clonidine or methyl-DOPA withdrawal any of which may induce catecholamine release. In fact, large plasma catecholamine surges, such as in a pheochromocytoma regularly elicit large renal renin release which then becomes a large factor in causing this hypertension and a target for drug treatment. The pharmacologic probes employed in this second step are most preferably I.V. phentolarnine with esmolol, to achieve combined alpha and beta blockade or alternatively most preferably I.V. labetalol, a combined alpha-beta blocker. A large blood pressure response implicates a neural factor, (e.g., a pheochromocytoma). If the above syndromes are clinically unlikely, pharmacologic testing for catecholamine involvement may be deferred or omitted.

In a preferred embodiment, the next drug testing step evaluates the involvement of the sodium-volume factor by administering most preferably I.V. furosemide and observing the blood pressure response to an induced natriuresis over the ensuing several hours. (See Table 11 below.) This testing may be superimposed on the presence of continued anti-renin drug therapy as indicated from step one especially if full dose R drug therapy was only partially effective.

The response or lack of it to these pharmiacologic probes, together with returned results of the baseline plasma renin testing (usually available within 24 hrs), enables assessment of the strength of the renin or sodium-volume factor and thereby informs the pathophysiologic basis for the hypertension. Thus, the response to these drug types informs the diagnosis—diagnosis ex juvantibus. For partial responders, just as in treating office or clinic patients, follow-up renin testing can inform the correct second or third drug choice.

Thus, the Laragh Method allows the physician to make a tentative categorical diagnosis of the underlying cause of the hypertensive crisis i.e., that the crisis is a result of the renin vasoconstrictor mechanism or the sodium-volume pressor mechanism. This tentative categorical diagnosis may be confirmed upon obtaining the PRA level results.

TABLE 11

PREFERRED PHARMACOLOGIC PROBES FOR IMPLEMENTING THE LARAGH METHOD FOR RAPID VASOCONSTRICTION (I.E., RENIN-ANGIOTENSIN OR CATECHOLS) OR SODIUM INVOLVEMENT IN THE HYPERTENSIVE CRISIS
The diagnostic approach (diagnosis ex juvantibus)

|   |   | Initial Dose | Repeat Dose | Onset of Drug |
|---|---|---|---|---|
| 1. | Anti-renin drug |   |   |   |
|   | Enalaprilat | 1.25 mg I.V. bolus | 2.5–10 mg 9–30 min | 10–15 min |
| 2. | Anti Sympathetic |   |   |   |
|   | Labetalol or | 20 mg I.V. bolus | 20–80 mg | 5 min |
|   | Phentolamine plus | 0.5–1.0 mg I.V. or 1 mg/min | 1–5 mg/min | 1–2 min |
|   | Esmolol (Brevibloe) | 0.1 ng/kg/min |   |   |
| 3. | Anti-sodium-volume |   |   |   |
|   | Furosemide | 20–40 mg I.V. Bolus | 80–200 mg | 5 min |

Interactive Formats

In another embodiment, the Laragh Method may be used in an interactive format via, for example, an internet website or computer program. Such an interactive format may be configured to accept patient information such as patient history, clinical characteristics, blood pressure, and lab values. This embodiment of the Laragh Method can be configured to be able to deliver, almost instantly, diagnostic and treatment recommendations such as, for example, lab tests and drugs as described above. The interactive nature of such a website allows much of the interviewing of patients and the input of clinical data to be carried out by nurse practitioners or by other physician extenders, thus freeing the physician from these time-consuming tasks and reducing the overall cost of treatment.

A further benefit of an interactive format embodiment of the Laragh Method is the ability of this format to compile extensive patient data. Such compilations may be helpful in further diagnosis and treatment recommendations and maintenance.

As a specific example of an interactive format, a computer program queries a user for patient information, such as blood pressure, previous treatments and PRA lab values, among other information. The program may then process this information and recommend a course of treatment based on the Laragh Method as described herein. The computer program may then compile the information entered, recommendations made and results obtained for one or more patients to provide useful data. The computer program may be made available in a computer readable format via, for example, a disk, CD ROM or internet website.

Conclusion

Awareness and understanding of baseline ambulatory plasma renin levels and various meaningful plasma renin response patterns to antihypertensive drugs helps the physician to find the simplest, most rational, "best fit," drug, or drug program, for each individual patient. A goal is to use one drug instead of two, or two instead of three, for the long-term commitment that hypertension mandates. Thus, the Laragh Method directs that a little extra time be spent at the beginning to work out the best drug fit program for each patient which can have big payoffs in efficacy, simplicity, cost, and compliance. In the long term, appropriate treatment ultimately may prevent serious, often fatal cardiovascular events, not to mention the physician and patient gratifications inspired by their mutual involvement in a rational treatment process.

The Laragh Method described herein enables the physician to determine the simplest and best drug treatment program for each patient. This system guides a decision tree for untreated new hypertensive patients as well as for the hypertensive patient who is already on drugs, but whose blood pressure is either not successfully treated, or whose medication should be changed, for clinical reasons, including unwanted side effects, or because the complexity of the regimen has led to non-compliance. In addition, the Laragh Method may be applied to the evaluation and treatment of hypertensive crises. The Laragh Method has been described herein in a number of specific examples. One skilled in the art will understand that some of the specifics of the examples can be varied to still apply the method and exploit its superior results.

What is claimed is:

1. A method for evaluating and treating a patient experiencing a hypertensive crisis comprising:
   a. obtaining a baseline laboratory profile comprising collecting blood from the patient to determine the patient's baseline plasma renin activity (PRA) level;
   b. (i) administering at least one anti-renin drug, and if the patient's blood pressure does not respond after (b)(i), (ii) administering at least one anti-volume drug;
   c. establishing a tentative categorical diagnosis based on the response in steps b(i) and/or b(ii); and
   d. confirming the categorical diagnosis after obtaining the results of the patient's baseline PRA level.

2. The method of claim 1, wherein the laboratory profile further comprises obtaining a CBC.

3. The method of claim 2, wherein the laboratory profile further comprises obtaining a plasma catecholamine profile and an electrolyte profile.

4. The method of claim 3, wherein the laboratory profile further comprises obtaining the results of an ECG and an echocardiogram.

5. The method of claim 1, further comprising administering a drug which allows quantifunction of a neural factor.

6. The method of claim 5, wherein the drug is selected from the group consisting of phentolamine, esprodol, and labetalol, or any combination thereof.

7. The method of claim 1 wherein the anti-renin drug is selected from the group consisting of captopril and enlaprilet or a combination thereof.

8. The method of claim 7, wherein the anti-volume drug is furosemide.

9. The method of claim 5, wherein the neural factor is selected from the group comprising pheochromocytoma, cocaine abuse, and clonodine withdrawal.

10. The method of claim 1, further comprising administering a non-specific vasodilator.

11. The method of claim 10, wherein the non-specific vasodilator is selected from the group consisting of nicardipine, verapamil, nitroprusside, nitroglycerin, hydralazine, diazaoxide, or any combination thereof.

12. A method of evaluating and treating a patient experiencing a hypertensive crisis caused by a bleeding state, said method comprising:

a. obtaining a baseline laboratory profile comprising:

(1) collecting blood from the patient to determine the patient's baseline PRA level; and (2) performing at least one diagnostic test which suggest the presence of a bleeding state;

b. administering a beta blocker; and c. confirming the diagnosis of the bleeding state by obtaining PRA results consistent with said diagnosis.

13. The method of claim 12, wherein the bleeding state is selected from the group consisting of cerebral dissection, aortic dissection, and acute myocardial infarction.

* * * * *